United States Patent [19]

Greenberg et al.

[11] Patent Number: 5,064,659

[45] Date of Patent: Nov. 12, 1991

[54] REACTIVE SUGARS FOR PROTECTION AGAINST CYANIDE ADULTERATION

[75] Inventors: Michael J. Greenberg, Northbrook, Ill.; Roy L. Whistler, West LaFayette, Ind.

[73] Assignee: Northwestern Chemical Company, West Chicago, Ill.

[21] Appl. No.: 526,175

[22] Filed: May 21, 1990

[51] Int. Cl.$^5$ ............................................. A23G 3/30
[52] U.S. Cl. ...................................... 426/3; 426/271; 426/321; 426/658; 426/660; 426/590; 426/5; 424/48
[58] Field of Search ................... 426/3, 660, 590, 658, 426/271, 321; 424/48

[56] References Cited

U.S. PATENT DOCUMENTS

| | | | |
|---|---|---|---|
| 3,429,716 | 2/1969 | Andrews | 426/545 |
| 4,048,299 | 9/1977 | Litchfield et al. | 426/3 |
| 4,157,401 | 6/1979 | Stroz et al. | 426/4 |
| 4,241,091 | 12/1980 | Stroz et al. | 426/4 |
| 4,378,374 | 3/1983 | Reggio et al. | 426/3 |
| 4,476,142 | 10/1984 | Netherwood | 426/3 |
| 4,479,969 | 10/1984 | Bakal et al. | 426/3 |
| 4,525,363 | 6/1985 | D'Amelia et al. | 426/3 |
| 4,695,463 | 9/1987 | Yang et al. | 426/3 |

FOREIGN PATENT DOCUMENTS 041598 12/1971 Japan .
055382 11/1982 Japan .

OTHER PUBLICATIONS

Blazer, R. M. and Whaley, T. W., "A Carbon-13 Nuclear Magnetic Resonance Spectroscopic Investigation of the Kiliani Reaction," *Journal of the American Chemical Society*, vol. 102, No. 15 (1980), pp. 5082-5085.

Serianni, A. S., Nunez, H. A., Barker, R., "Carbon-Enriched Carbohydrates, Preparation of Aldononitriles and Their Reduction with a Palladium Catalyst," *Carbohydrate Research*, vol. 72 (1979), pp. 71-78.

Serianni, A. S., Nunez, H. A., Barker, R., "Cyanohydrin Synthesis: Studies with [$^{14}$C]-Cyanide," *Journal of Organic Chemistry*, vol. 45, No. 16 (1980), pp. 3329-3343.

Varma, R. and French, D., "Mechanism of the Cyanohydrin (Kiliani-Fischer) Synthesis," *Carbohydrate REsearch*, vol. 25 (1972), pp. 71-79.

*Primary Examiner*—Jeanette Hunter
*Attorney, Agent, or Firm*—Willian Brinks Olds Hoffer Gilson & Lione

[57] ABSTRACT

Cyanide reactive reducing sugars, such as xylose, ribose, arabinose, glyceraldehyde and erythrose, are added to a food, drug or other oral composition to detoxify cyanide. The cyanide reacive reducing sugar is added in an amount in excess of about 1 weight percent. The cyanide reactive reducing sugar may be mixed into the composition or may be applied as a coating on a solid composition. The cyanide reactive reducing sugar is one of the edible components of the gum.

13 Claims, No Drawings

REACTIVE SUGARS FOR PROTECTION AGAINST CYANIDE ADULTERATION

FIELD OF THE INVENTION

The present invention relates to the detoxification of cyanide in foods, drugs or other oral compositions before or during consumption for the purpose of minimizing injury to consumers who consume cyanide-adulterated products.

BACKGROUND OF THE INVENTION

Cyanide is a readily available poison which is extremely dangerous and often fatal when consumed in relatively small dosages. The presence of cyanide in foods is difficult to detect since it does not possess an easily noticeable color. At low doses and in the presence of other flavors, cyanide may not be detected by its bitter almond odor.

Packaging devices have been provided which warn a consumer of potential tampering or adulteration of the packaged products. These systems generally involve a physical modification of the package such as the presence of a plastic seal which when broken indicates tampering. However, if the warning signal given by the package is overlooked by the consumer or circumvented by the tamperer such as by injection, the consumer would still ingest the cyanide-laced product.

Sugars or saccharides are frequently added to food. Among the most commonly used sugar additives are glucose and fructose. Other edible sugars, including xylose, ribose, arabinose, glyceraldehyde and erythrose, are occasionally found in or added to food.

For example, Ogawa (Japanese Patent No. Sho 82-55382) describes a method for preparing chewing gum which utilizes xylose reacted with an amino acid and blended at a temperature of at least 100° C., to produce Maillard reaction products for improved flavor. Ogawa teaches flavor impairment if the level of the Maillard reaction product exceeds 2%, although a level of up to 5% is also mentioned.

Yamada (Japanese Patent No. Sho 71-41598) discloses improved taste, color and fragrance of alcoholic beverages by adding a minor amount of xylose instead of glucose. Yamada teaches a maximum concentration of 3% weight per volume for xylose.

Andrews (U.S. Pat. No. 3,429,716) discloses the use of tetroses, pentoses and hexoses having two "hydroxyl groups in the cis position on the 2,3 carbons" of the ring structures, particularly erythrose, ribose, allose and gulose. These sugars are added at a concentration between about 0.0005% and 0.001% to retard the oxidation of food compounds. Andrews reports that arabinose or xylose are ineffective in retarding oxidation and that glyceraldehyde accelerates oxidation.

Sodium cyanide and potassium cyanide are commercially available and extremely poisonous compounds. Death may occur in the presence of only 50 milligrams of sodium or potassium cyanide in food products. Individual responses to cyanide poisoning vary widely. Some persons have survived doses of more than three grams. Once cyanide is ingested, it must be absorbed from the gut into the bloodstream and thence into the body tissues where it poisons cell respiration. Cyanide is one of the most rapidly acting poisons: victims have died within minutes of exposure. Rapid treatment using appropriate antidotes, such as amyl nitrite ($C_5H_{11}ONO$), greatly increases the chance for survival.

Lower doses of cyanide allow more time for successful treatment to begin, sometimes more than one hour. Thus, there may be some benefit to reducing the level of cyanide ingested even though the dosage may still be lethal without treatment. In addition detoxification of cyanide in the gut would prevent absorption of and ill effects from cyanide.

It is therefore an object of the present invention to add an ingestible component to foods, drugs and other oral compositions which will reduce toxicity due to cyanide adulteration.

SUMMARY OF THE INVENTION

In accordance with one embodiment of the present invention, there is provided a food, drug or other oral composition which includes ingestible ingredients and a cyanide reactive reducing sugar. A reducing sugar is one having an aldose function. A cyanide reactive reducing sugar is defined as any aldose which reacts with cyanide faster than glucose at room temperature in aqueous solution. The cyanide reactive reducing sugar is present in an amount greater than about 1 weight percent.

In accordance with another embodiment of the present invention, there is a method of manufacturing a food, drug or other oral composition which is capable of detoxifying an adulterating amount of cyanide. The method includes the step of adding a cyanide reactive reducing sugar to the food in an amount in excess of 1 weight percent.

PRESENTLY PREFERRED EMBODIMENTS

In accordance with the present invention, it has been discovered that certain reducing sugars can be employed to detoxify or neutralize cyanide in food, drug or other oral compositions. As used herein the term food, drug or oral composition means any ingestible product or products intended to be taken into the mouth. Such compositions include any food, drug or like composition intended for contact with the oral cavity. Accordingly, the food or oral composition may be chewed, swallowed, allowed to dissolve, or swirled about in the oral cavity such that at least a portion of the composition is likely to enter the digestive tract. Examples of materials suitable for use with the present invention would include foods, beverages, nutritional supplements, chewing gums, oral medications, toothpastes and mouthwashes.

Preferably, the reducing sugar is present in the food, drug or oral composition in an amount sufficient to detoxify the anticipated quantity of cyanide adulteration. Although the sugar is thought to combine with cyanide on a one-for-one molar basis, the inclusion of an excess of reducing sugar is preferred to encourage more rapid and complete detoxification of the cyanide. A sufficient quantity of reducing sugar should be used such that the anticipated cyanide will be completely or substantially destroyed before the product would be consumed. Alternatively, if the consumable product is of such low moisture that detoxification during storage is likely to be incomplete, sufficient reducing sugar should be used to ensure rapid total or substantial detoxification of the anticipated cyanide level while the cyanide is still in the mouth or gut. This would help decrease or prevent toxicity.

Many factors affect the required amount of reducing sugar, including the reactivity of the sugar, the anticipated level and method of cyanide adulteration, the moisture level of the product and the anticipated storage interval between adulteration and consumption. Not only could the nature of the product itself affect the required level, but the method of incorporating the cyanide reactive reducing sugar could, too. Where the oral composition is in liquid or solid form, the cyanide reactive reducing sugar may be mixed into the composition at virtually any step in manufacture. If the oral composition is a solid, and adulteration by surface application is anticipated, the reducing sugar may be added to the oral composition by surface application as a coating.

When utilized in most food products, the cyanide reactive reducing sugars are preferably present in an amount of from about 1 percent by weight of the composition to about 50% or more. A preferred concentration of the cyanide reactive reducing sugar is about 4–20%. A more preferred concentration of the cyanide reactive reducing sugar is at least 5 percent. A higher level of cyanide reactive reducing sugar may be preferred when the reducing sugar is mixed into the product than when it is applied to the surface. For mixing into beverages, a level of about 15% is preferred. Higher levels of cyanide reactive reducing sugars may be used as long as there are no deleterious effects on food quality.

It has been discovered that several uncommon sugars will quickly detoxify cyanide. This phenomenon occurs when they are incorporated into a food beverage or drug product at appropriate levels. Detoxification of cyanide occurs during storage or even upon consumption, but before toxicity is manifested. The preferred sugars are xylose ribose and arabinose. Other sugars such as glyceraldehyde and erythrose may be expected to be similarly effective. These sugars are typically characterized by aldose functionality and a length of three to five carbons. Most preferred is xylose. If xylose is applied to the surface of the product, as little as 1% by weight may be effective. More preferably, about 2% to about 5% xylose by weight is applied to the surface.

It is believed that one possible mechanism of cyanide detoxification involves converting cyanide to non-toxic amides and acids through an aldonitrile intermediate as shown below for ribose:

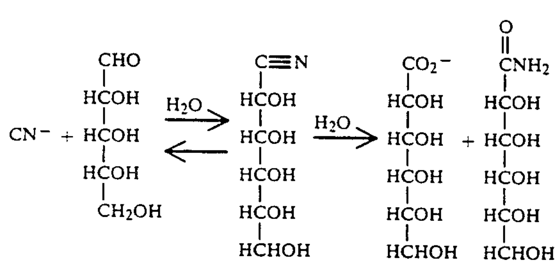

The following examples are merely intended to illustrate the present invention. It is to be understood that these examples are not to be construed as a limitation of the present invention, the scope of which is defined in the appended claims.

EXAMPLES

Example 1

A dilute solution (0.2 M) of potassium cyanide was prepared with radiolabelled ($C^{13}$) potassium cyanide. Solutions of the following sugars (2.0 M) were prepared: fructose, glucose, arabinose, ribose, and xylose. Equal volumes of potassium cyanide and reducing sugar solution were mixed and analyzed continuously for $C^{13}$-labelled cyanide using nuclear magnetic resonance. Data were tabulated for each reducing sugar. For each sugar, a half-life, or time required for half of the cyanide to be destroyed, was determined and reported below:

| Sugar | Cyanide Half-Life (25° C.) |
|---|---|
| Fructose | 63.9 min |
| Glucose (Dextrose) | 19.3 min |
| Arabinose | 4.2 min |
| Ribose | <4 min |
| Xylose | 1.0 min |

This experiment indicates that soft drinks powdered drink mixes, and milk can be protected by using arabinose, ribose and/or xylose as the primary or sole sweetener(s). The levels used would be equivalent to a liter of beverage containing 15% sugar being adulterated with 6.5 g of potassium chloride. Using the reactive sugars, the cyanide level in an eight-ounce serving would drop to a sublethal level in approximately 5 to 30 minutes. With conventional sweeteners, such as fructose, glucose and sucrose (which is a non-aldose combination of fructose and glucose which would be expected to react even more slowly). the beverage would remain lethal for 2 to 7 hours or longer.

These data also suggest that a small dose of dry cyanide taken with xylose would be significantly detoxified in saliva, but detoxification with sucrose, glucose or fructose would be minimal.

Example 2

Standard size (3 g) sticks of chewing gum were prepared and dusted with sucrose. One half of the sticks were designated controls and received no xylose. To each side of the remainder of the sticks. 50 mg of xylose powder was applied. To both control and xylose-coated sticks, powdered potassium cyanide was applied. 25 mg to each side. Next, all sticks were wrapped in a conventional tissue/foil laminated wrapper and a paper sleeve. The gum sticks were stored at 85° F. and 50% relative humidity for 0.5 and 7.0 days. At each time, one half of the sticks were analyzed for cyanide. The xylose-coated gum had lost 51% and 89% of the original cyanide content after 0.5 and 7.0 days in storage, respectively. The control gum lost 35% and 61% of the original cyanide content during the same time periods.

Example 3

Sticks of gum were prepared as described in Example 2. except for a change in cyanide application. The sticks were treated with an aqueous solution of 50% potassium cyanide, instead of powdered potassium cyanide. Enough cyanide solution was applied to deposit 25 mg of potassium cyanide on each side of the gum sticks. The sticks were analyzed after 1.0, 3.0 and 24.0 hours. At these times, the xylose gum had reduced the cyanide level by 59%, 94% and 100% respectively. Cyanide levels in the control gum were reduced by 40%, 70% and 90% for the same time periods. Calculations using first order kinetic equations show that the xylose-coated gum could be expected to completely detoxify the cyanide in less than five hours compared to 51 hours for the control gum.

While reference has been made to certain specific food materials, it is realized that this invention is applicable to the full range of foods, cosmetics and pharmaceuticals in aqueous and so-called non-aqueous or essentially anhydrous systems, wherever an oral composition may be adulterated.

We claim:

1. A method of making a food, drug or other oral composition which is capable of neutralizing a later added cyanide adulterant, said composition containing ingestible ingredients, said method comprising:
    mixing the ingredients of said composition; and
    adding to the ingredients an effective amount of a cyanide reactive agent, said amount being sufficient to neutralize the cyanide promptly, said agent comprising a three-to-five-carbon sugar which has an aldose functionality.

2. The method of claim 1 wherein said composition is a liquid.

3. The method of claim 1 wherein said composition is a solid.

4. The method of claim 3 wherein said solid composition is coated with said sugar.

5. The method of claim 1 wherein said sugar is present at a level of at least 1 weight percent of said composition.

6. The method of claim 1 wherein said sugar is selected from the group consisting of xylose, ribose, arabinose, glyceraldehyde, erythrose and combinations thereof.

7. The method of claim 1 wherein said sugar is present at a level of at least 5 weight percent of said composition.

8. The method of claim 1 wherein said sugar is present at a level of at least 15 weight percent of said composition.

9. A method of manufacturing a chewing gum capable of neutralizing a later added cyanide adulterant, comprising the following steps:
    providing chewing gum ingredients, said ingredients comprising a gum base, a softener, a sweetener and flavoring compounds; and
    adding to the ingredients a three-to-five-carbon sugar which has an aldose functionality, said sugar being added at a level of at least 1 weight percent of the chewing gum.

10. The method of claim 9 wherein the sugar is mixed into the chewing gum ingredients at a level of at least 3 weight percent of the chewing gum.

11. The method of claim 9 wherein the chewing gum is coated with said sugar, said sugar being present at a level of at least 1 weight percent of the chewing gum.

12. An oral composition, comprising consumable ingredients susceptible to cyanide tainting, which is rendered capable of neutralizing a later added cyanide contaminant by the addition thereto of a cyanide reacting agent in the amount of at least 1 weight percent of the oral composition, said agent comprising a three-to-five-carbon sugar which has an aldose functionality.

13. A method of making a food, drug or other oral composition which is capable of neutralizing a later added cyanide adulterant, said composition containing ingestible ingredients, said method comprising:
    mixing the ingredients of said composition; and
    adding to the ingredients an amount of a cyanide reactive agent sufficient to constitute at least about 1 weight percent of said composition, said agent comprising a three-to-five-carbon sugar which has an aldose functionality.

* * * * *

UNITED STATES PATENT AND TRADEMARK OFFICE
CERTIFICATE OF CORRECTION

PATENT NO. : 5,064,659
DATED      : November 12, 1991
INVENTOR(S): Michael J. Greenberg et al.          Page 1 of 3

It is certified that error appears in the above-identified patent and that said Letters Patent is hereby corrected as shown below:

Title page, item [73], after "Assignee" please delete "Northwestern Chemical Company" and substitute therefor --Northwestern Flavors, Inc.--.

Title page, item [56], under the heading "OTHER PUBLICATIONS", on line 4, before "102" please delete "vol." and substitute therefor --Vol.--; lines 5 and 6, delete "Carbon-Enriched" and substitute therefor --Carbon-13-Enriched--; line 8, before "72" delete "vol." and substitute therefor --Vol.--; and after "71-78." insert --(Serianni I)--; line 11, before "45" delete "vol." and substitute therefor --Vol.--; line 12, please delete "3329-3343" and substitute therefor --3329-43. (Serianni II)--; and lines 14 and 15, please delete "REsearch, vol." and substitute therefor --Research, Vol.--.

On the title page, after "Attorney, Agent, or Firm", please delete "Hoffer" and substitute therefor --Hofer--.

UNITED STATES PATENT AND TRADEMARK OFFICE
CERTIFICATE OF CORRECTION

PATENT NO. : 5,064,659

DATED : November 12, 1991

INVENTOR(S) : Michael J. Greenberg et al.   Page 2 of 3

It is certified that error appears in the above-identified patent and that said Letters Patent is hereby corrected as shown below:

On the title page, line 4 of the Abstract, please delete "reacive" and substitute therefor --reactive--.

In column 1, line 39, please delete "100°C.," and substitute therefor --100°C--.

In column 1, line 67, after "poisons" please delete ":" and substitute therefor --;--.

In column 2, line 7, after "addition" please insert --,--.

In column 2, line 50, before "chewing" please delete "." and substitute therefor --,--.

In column 3, line 4, after "product" please insert --,--.

In column 3, line 18, please delete "percent" and substitute therefor --%--; line 22, please delete "percent" and substitute therefor --%--.

In column 3, line 5, after "food" please insert --,--; line 9, after "xylose" please insert --,--.

UNITED STATES PATENT AND TRADEMARK OFFICE
CERTIFICATE OF CORRECTION

PATENT NO. : 5,064,659
DATED : November 12, 1991
INVENTOR(S) : Michael J. Greenberg et al.

It is certified that error appears in the above-identified patent and that said Letters Patent is hereby corrected as shown below:

In column 4, line 16, second heading in the table, please delete "25°C." and substitute therefor --25°C--.

In column 4, line 24, after "drinks" please insert --,--; line 35, after "slowly)." insert --,--.

In column 4, line 46, after "sticks," please insert --,--; line 48, after "applied." insert --,--; line 51, delete "85°F." and substitute therefor --85°F--.

In column 4, line 61, after "2." please insert --,--.

IN THE CLAIMS

In claim 9, line 3, after "steps" please delete ";" and substitute therefor --:--.

Signed and Sealed this

Twelfth Day of October, 1993

*Attest:*

BRUCE LEHMAN

*Attesting Officer*   *Commissioner of Patents and Trademarks*